(12) United States Patent
Portney (10) Patent No.: US 7,204,849 B2
(45) Date of Patent: Apr. 17, 2007

(54) NARROW PROFILE INTRAOCULAR LENS (76) Inventor: Valdemar Portney, 11940 N. Riviera, Tustin, CA (US) 92782

( * ) Notice: Subject to any disclaimer, the term of this patent is extended or adjusted under 35 U.S.C. 154(b) by 191 days.

(21) Appl. No.: 10/444,896

(22) Filed: May 24, 2003

(65) Prior Publication Data
US 2003/0199976 A1    Oct. 23, 2003

Related U.S. Application Data (63) Continuation-in-part of application No. 09/809,152, filed on Mar. 15, 2001, now Pat. No. 6,596,025.

(51) Int. Cl.
A61F 2/16    (2006.01)
(52) U.S. Cl. .................... 623/6.17; 623/6.18
(58) Field of Classification Search ........... 623/6.17, 623/6.18, 6.19, 6.23–6.28
See application file for complete search history.

(56) References Cited

U.S. PATENT DOCUMENTS

| 4,504,982 | A | * | 3/1985 | Burk | 623/6.23 |
| 4,898,461 | A | * | 2/1990 | Portney | 351/169 |
| 5,755,786 | A | * | 5/1998 | Woffinden et al. | 623/6.17 |
| 6,015,435 | A | * | 1/2000 | Valunin et al. | 623/6.28 |
| 6,162,249 | A | * | 12/2000 | Deacon et al. | 623/6.16 |
| 6,468,306 | B1 | * | 10/2002 | Paul et al. | 623/6.16 |
| 2003/0144733 | A1 | * | 7/2003 | Brady et al. | 623/6.16 |
| 2004/0059414 | A1 | * | 3/2004 | Green | 623/6.16 |
| 2004/0230299 | A1 | * | 11/2004 | Simpson et al. | 623/6.11 |

* cited by examiner

Primary Examiner—Corrine McDermott
Assistant Examiner—Cheryl Miller
(74) Attorney, Agent, or Firm—Walter A. Hackler (57) ABSTRACT A narrow profile, glare reducing, posterior chamber intraocular lens comprises an optic having an anterior surface and a posterior surface and an optical axis. The posterior surface is formed having two adjacent peri-axial, stepped imaging zones, the two imaging zones having the substantially the same optical power. A transition zone between the two imaging zones preferably has a surface of continuous curvature shaped to reduce direct glare from light incident on the transition zone in an individual's eye in which the intraocular lens is implanted by internal reflection of direct light incident on the transition zone. Attachment members joined to the optic position the intraocular lens in an eye with the optical axis of the optic generally aligned with the optical axis of the eye. In variations, the transition zones are formed at the optic edge to minimize direct and indirect in the eye of an individual wearing the intraocular lens.

4 Claims, 7 Drawing Sheets

NARROW PROFILE INTRAOCULAR LENS

This application is a continuation-in-part of application Ser. No. 09/809,152, filed Mar. 15, 2001, now U.S. Pat. No. 6,596,025.

BACKGROUND OF THE INVENTION

1. Field of the Invention

The present invention relates generally to the field of ophthalmic devices, more particularly to intraocular lenses (IOLs), and still more particularly to thin profile monofocal refractive IOLs for implanting in narrow ocular regions, especially the anterior chamber of an eye.

2. Background Discussion

The following definitions are considered helpful to the understanding of the present invention:

The term "phakic" applies to an eye in which the natural crystalline lens is still present.

The term "aphakic" applies to an eye from which the natural crystalline lens has been surgically removed, for example, due to the formation of cataracts on the lens.

The anterior chamber of an eye is the narrow region between the back, endothelial surface of the cornea and the front surface of the iris.

The posterior chamber of a phakic eye is the narrow region between the back surface of the iris and the front surface of the natural crystalline lens.

A Fresnel lens (as defined at page 167 of the DICTIONARY OF OPTICS, published by Butterworth Heinemann, 1995) is "A lens surface of narrow concentric rings or prism sections of a specified power that gives the effect of a continuous lens surface with the same power, but without the usual thickness and weight.

Glare (as defined at page 53 of THE GLOSSARY OF OPTICAL TERMINOLOGY, published by Professional Press Books, Fairchild Publications, 1986) is "Any degree of light falling on the retina in excess of that which enables one to see clearly." And alternatively as "Any excess of light which hinders rather than helps vision. (Too much light in the wrong place.)"

Vision in a phakic eye is caused by light from a viewed object being refracted by the cornea and the natural crystalline lens to form an image on the retina at the back of the eye. Corrective spectacles, contact lens or corneal reshaping may be used to assist such image formation. Optical muscles connected to a normal crystalline lens change the shape of the lens as needed to provide images of objects at different distances from the eye, an optical process known as accommodation.

The prevailing procedure for restoring vision (except for accommodation) in an aphakic eye is the surgical implanting of a refractive artificial lens, called an intraocular lens (TOL), ordinarily in the capsular bag from which the natural lens has been removed.

In addition to continued development of TOLs for restoring vision in aphakic eyes, considerable attention has recently been directed toward developing refractive IOLs (and insertion instruments) for implanting in the anterior chamber of phakic eyes having normal crystalline lenses to correct such vision defects as myopia, hyper-metropia, presbyopia and astigmatism. The implanting of such corrective IOLs can potentially eliminate the wearing of spectacles or contact lenses, and/or eliminate permanent surgical procedures involving the cornea.

Anterior chamber-type IOLs may alternatively be implanted in posterior chambers of phakic eyes for providing corrective power to the natural lens, as may be needed due to subsequent physiological changes of the natural lens as an individual ages.

The anterior chamber is generally dome-shaped and very narrow—typically only about 3 mm at its center. The posterior chamber of a phakic eye be even more narrow, depending upon the size of the crystalline lens and the amount of its accommodation the width of the posterior chamber of a phakic eye—the successful implanting of a corrective IOL in either of these ocular chambers is extremely difficult and risks injuring delicate ocular tissue, especially the cornea's endothelial surface in the case of anterior chamber implanting. Consequently, refractive corrective IOLs, particularly the IOL optics, are desirably made as thin as possible consistent with providing the requisite corrective power and structural stability of the optic.

To this end, several known patents disclose the use of a Fresnel lens on one surface of a refractive IOL optic. For example, U.S. Pat. No. 4,673,406 to Schiegel (issued Jun. 16, 1987) discloses a one-piece foldable refractive IOL with one surface of its central lens body formed as a Fresnel lens to reduce the thickness of the optic to enable the IOL to be implanted in a folded condition into an eye through a small corneal incision. The patent further discloses that individual zones of the multi-zone Fresnel lens are selected such that the focal points of all the zones coincide so as to reduce spherical aberration. As another example, U.S. Pat. No. 4,787,903 to Grendahl (issued Nov. 29, 1988) discloses a refractive IOL or corneal lens having an optic that incorporates a Fresnel lens with multiple, concentric ring-zones. The Grendahl lens is further disclosed as being made of a composite material that allows refractive index modification with electromagnetic energy. (The Grendahl patent asserts a first use of a Fresnel lens for IOLs or corneal lenses, the Grendahl patent application having been filed shortly before the Schiegel patent application was filed).

As still further examples, U.S. Pat. No. 4,846,833 to Cumming (issued Jul. 11, 1989) discloses the forming of a Fresnel lens on the back surface of a posterior chamber IOL so the Fresnel surface will be sealed by the posterior capsule surface upon the implanting of the IOL in an aphakic eye. U.S. Pat. No. 6,096,077 to Callahan et al. (issued Aug. 1, 2000) discloses a thin IOL having the posterior surface formed of a stepped series of annular concentric rings of increasing diameter surrounding a central planar disc region; although, the Callahan et al. patent does not specifically identify the IOL posterior surface as being a Fresnel lens, the associated figures indicate that such is the case.

A characteristic common to the four above-cited patents is that the Fresnel zones comprise a series of staircase-like concentric zones separated from one another by abrupt transition steps. None of the Specifications of the cited patents describe these transition steps, however the accompanying figures depict the transition steps as having flat transition surfaces that are parallel to one another and to the optical axis of the optic, as are all Fresnel lenses. Moreover, none of the above-cited patents disclose any glare effects that may be caused by the flat transition steps between Fresnel zones.

As shown below by the present inventor, IOLs having abrupt Fresnel zone transition steps with flat surfaces induce substantial distracting and potentially hazardous glare in the IOL wearer's eye when light (especially bright light) impinges on the lens optic as, for example, is commonly encountered in night driving or when driving into the sun.

Accordingly, a principal objective of the present invention is to provide a narrow profile (that is, thin) IOL, in particular, a narrow profile monofocal IOL that substantially minimizes such visual glare problems.

In addition to minimizing glare at imaging zone transition steps in thin IOLs it is desirable to minimize glare from IOL optic peripheral edges, while still maintaining thinness of the optic. In this regard it is known that a reduction on optic thickness can be achieved by reducing the optic diameter. However, optic diameter reduction may result in glare due to light passing outside the optic diameter. Such optic edge glare may be direct, indirect or combined direct and indirect glare according to lighting conditions encountered by an individual in whose eye the IOL is implanted. Indirect and direct glare are most likely to be encountered at night under driving conditions in which the IOL wearer encounters bright lights, such as streetlights, traffic lights and/or headlights and taillights on other vehicles and the individual's pupil diameter is large enough to expose regions outside the IOL optic diameter (as is likely under night driving conditions). The effects of such glare include halos around light sources and blurred vision.

A principal objective of the present invention is therefore to provide a narrow profile (thin) IOL having a large optic diameter peripheral edge region shaped to minimize direct and/or indirect glare caused by light impinging on the optic peripheral edge.

SUMMARY OF THE INVENTION

In accordance with the present invention, a narrow profile, glare reducing, posterior chamber intraocular lens comprises an optic having an anterior surface and a posterior surface and an optical axis. One of the anterior and posterior surfaces is formed having adjacent first and second peri-axial, stepped imaging zones, the second peri-axial imaging zone having the substantially the same optical power as the first peri-optical imaging zone.

A transition zone on the optic posterior surface between the first and second peri-axial imaging zones is formed having a surface of continuous curvature so as to reduce direct glare an individual's eye in which the intraocular lens is implanted by internal reflection of light rays incident on the transition zone.

Positioning means are joined to the optic for positioning the intraocular lens in the eye with the optical axis of the optic generally aligned with the optical axis of the eye.

The first peri-axial imaging zone may be circular in shape and be centered at the optical axis of the optic and may have a diameter between about 4.3 mm and about 4.5 mm. The second peri-axial imaging zone is in such case formed in annular ring around the first peri-axial imaging zone.

The first peri-axial imaging zone may be recessed in the optic relative to the second peri-axial imaging zone. Alternatively, the second peri-axial imaging zone may be recessed in the optic relative to the first peri-axial imaging zone.

In combination, the first and second peri-axial imaging zones and the transition zone define one surface, preferably the posterior surface, of the optic that has a preferred maximum thickness at any point of between about 0.30 mm and about 0.40 mm. Still preferably, the height of the transition zone, the surface of which may be generally S-shaped, is preferably between about 0.10 mm and about 0.40 mm and the width of the transition zone is preferably between about 0.15 mm and about 0.30 mm.

In accordance with other variations, there is provided a narrow profile, glare reducing intraocular lens comprising an optic having an anterior surface and a posterior surface, the optic having a peripheral edge and an optical axis. A transition zone is formed between the optic posterior surface and the optic peripheral edge, the transition zone having a surface of continuous curvature without any abrupt change so as to minimize direct glare in an individual's eye in which the intraocular lens is implanted by causing internal reflection of light impinging on the optic from a centrally located source of light and through the optic onto a substantial width of the transition zone. Included are positioning means joined to the optic for positioning the optic in individual's eye with the optical axis of the optic generally aligned with an optical axis of the eye.

The transition zone surface may have a continuously variable curvature so as to reduce both indirect and direct glare. Then optic posterior surface may be concave or convex shaped. The optic posterior surface may be formed having an imaging zone centered at the optical axis of the optic.

In another variation, a narrow profile, glare reducing intraocular lens comprises an optic having an anterior surface and a posterior surface, a peripheral edge and an optical axis. A transition zone formed between the posterior surface and the optic edge has a transition zone with a non-linear surface of continuously variable curvature shaped to minimize indirect glare created by a peripherally located source of light impinging through the optic on a substantial width of the transition zone in an individual's eye in which said intraocular lens is implanted. Positioning means are joined to the optic for positioning said intraocular lens in said eye with the optical axis of the optic generally aligned with an optical axis of the eye.

The optic posterior surface may be concave or convex shaped.

Thus, in one such variation intraocular lens, the transition zone surface has a continuous curvature that eliminates direct glare caused by diffraction and in another variation intraocular lens the transition zone has surface of variable curvature that that reduces glare caused by refraction.

BRIEF DESCRIPTION OF THE DRAWINGS

The present invention can be more readily understood by a consideration of the following detailed description when taken in conjunction with the accompanying drawings, in which.

In the various FIGS. the same elements and features are given the same reference numbers while corresponding features and elements are given the same reference number followed by the letters "a", "b", "c" and so forth as will be apparent.

DESCRIPTION OF THE PREFERRED EMBODIMENT

Glare caused by abrupt flat transition steps between Fresnel zones of lenses as disclosed in the above-cited patents, may be indirect, direct, or combined indirect and direct, according to lighting conditions encountered by an individual in whose eye the intraocular lens is implanted. Indirect and direct glare are most likely to be encountered at night under driving conditions in which the IOL wearer encounters bright lights, such as streetlights, traffic lights and/or headlights and taillights on other vehicles.

Figure 1:
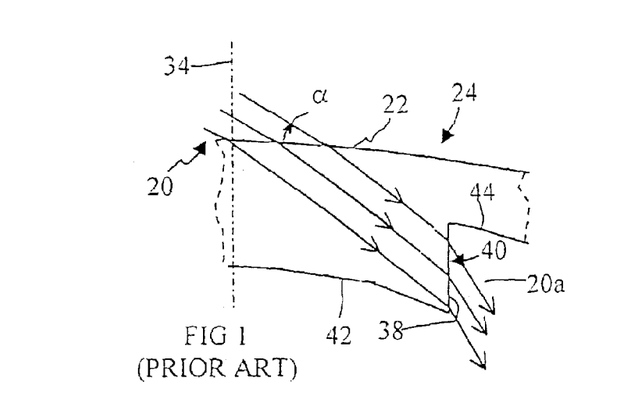
FIG. 1 is a partial cross sectional drawing of a representative prior art refractive intraocular lens employing a Fresnel lens on one surface of the optic, showing a sharp, flat step between a representative pair of adjacent Fresnel zones, showing several light rays obliquely incident on the front surface of the optic and showing the path of the light rays as they are refracted through the optic and out through the flat Fresnel zone step surface.
Figure 2:
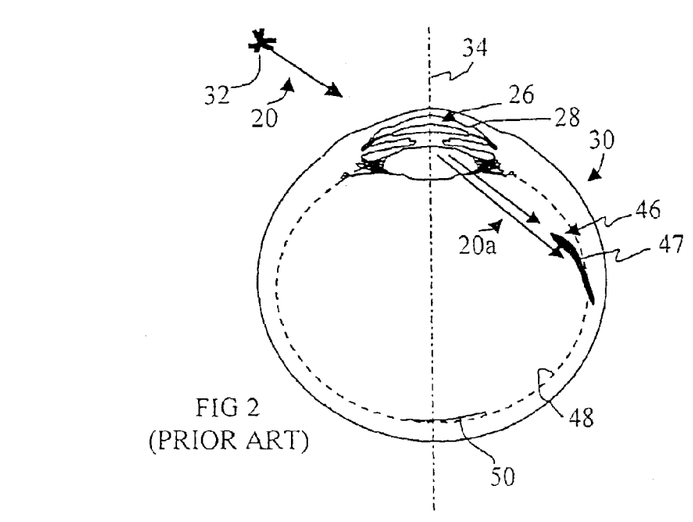
FIG. 2 is a cross sectional drawing of an eye in which the representative intraocular lens of FIG. 1 is implanted in the anterior chamber, and depicting a typical strong indirect glare pattern formed on a peripheral region of the eye's retina by the light rays that are obliquely incident on the sharp, flat Fresnel zone step as depicted in FIG. 1.

FIGS. 1 and 2 illustrate the indirect glare that may, for example, be caused by lights encountered in night driving or by the sun in daylight driving. In FIG. 1, parallel light rays 20 are shown impinging at an oblique angle, α, on a front surface 22 of part of an optic 24 that has a Fresnel lens formed on the back surface. Optic 24 is part of a representative prior art IOL 26 that has been implanted in the anterior chamber 28 of an eye 30 (FIG. 2). Light rays 20 may, for example, originate from a bright streetlight 32 that is out of the direct line of vision 34 of eye 30.

As shown in FIG. 1, light rays 20 are refracted, in accordance with Snell's Law, as they enter, pass through and exit optic 24. Light exits optic 24 as parallel rays 20a from a flat surface 38 of an abrupt Fresnel zone step 40 between adjacent stepped Fresnel zones 42 and 44. Similar oblique light refraction will occur at other abrupt, flat step surfaces (not shown) between other adjacent pairs of Fresnel zones (also not shown). (Viewed image light rays are not shown to avoid confusion.)

Within eye 30 light rays 20a refracted from flat Fresnel zone step surface 38 (as well as light rays refracted from other abrupt flat Fresnel zone step surfaces) of optic 24 impinge on a region 46 of retina 48 (shown in broken lines) to cause a bright glare pattern 47 (indicated by a bold, dark shading). The location of retinal glare pattern 47 depends upon the oblique light angle, α, of incidence on optic 24, but is typically outside a normal viewed image region 50 of retina 48 in a light-sensitive rod region of the retina.

Indirect glare, especially sudden bright glare, in peripheral retinal region 46 can be extremely distracting to the individual in which IOL 26 is implanted, and in night driving can cause driver confusion and make driving dangerous.

Figure 3:
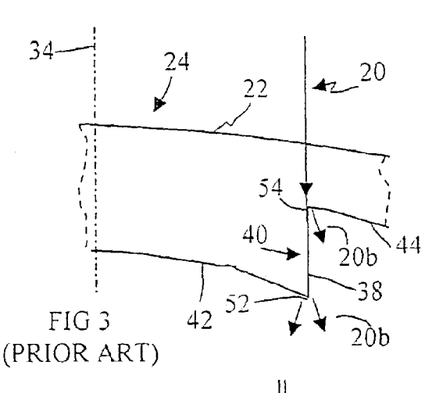
FIG. 3 is a partial cross sectional drawing, similar to FIG. 1, of a representative prior art refractive intraocular lens employing a Fresnel lens on one surface of the optic, showing a sharp, flat step between a representative pair of adjacent Fresnel zones, showing a single light ray perpendicularly incident on the front surface of the optic and showing the path of the light ray as it is refracted through the optic and is diffracted out of the optic at sharp corners of the sharp, flat Fresnel zone step surface.
Figure 4:
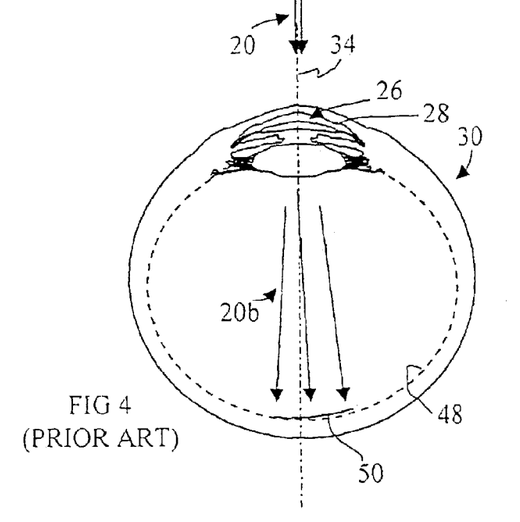
FIG. 4 is a cross sectional drawing of an eye, similar to FIG. 2, in which the representative intraocular lens of FIG. 3 is implanted in the anterior chamber, and depicting the manner in which a direct glare pattern is formed at the image region of the retina by the diffracted light from the intraocular lens Fresnel zone step as depicted in FIG. 3.

Furthermore, as depicted in FIGS. 3 and 4, sharp corners 52 and 54 of Fresnel zone step 40 (and sharp corners of other Fresnel zone steps of optic 24) cause direct (diffractive) glare. As an illustration, a single light ray 20 shown in FIG. 3 impinging perpendicularly on front surface 22 of optic 24 is diffracted into diverging rays 20b by sharp corners 52 and 54 of representative Fresnel zone step 40 between Fresnel zones 42 and 44. Added light diffraction is caused by corresponding sharp corners of other Fresnel zone steps between other adjacent pairs of Fresnel zones (not shown) of optic 24. (Viewed image light rays are not shown to avoid confusion.)

Scattered rays 20b in eye 30 that impinge on vision region 50 of retina 48 (FIG. 4) cause, most noticeably at night, visual light effects around or at viewed street, traffic, vehicle and other bright lights. These light effects may, for example, be in the form of bright star bursts, streamers or halos (not shown), depending upon ambient light conditions causing the diffractive light scattering by corners of Fresnel zone steps of IOL optic 24. At night these light effects caused by light diffraction at corners of abrupt Fresnel zone steps, like step 40, can be extremely distracting and can make driving in busy traffic dangerous due to their image blurring.

Thus, depending upon light conditions, abrupt Fresnel zone step 40 with flat surface 38 on IOL optic 24 may cause either indirect (refractive) or direct (diffractive) glare, or both types of glare at the same time, in eye 30 of an individual in whom IOL 26 is implanted.

As described hereinbelow, the present inventor has determined that such glare can be substantially reduced by forming a non-abrupt, curved transition zone between adjacent imaging zones.

Figure 5:
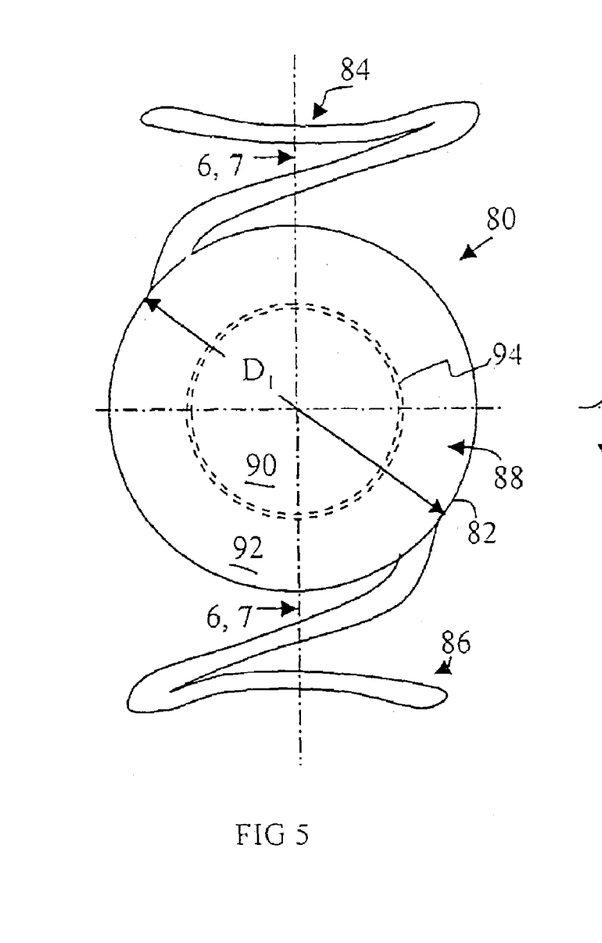
FIG. 5 is a plan view of the posterior (back) surface of an intraocular lens of the present invention, showing the optic and an opposing pair of fixating members, showing a first, central imaging zone surrounded by a second imaging zone, and showing in dashed lines the transition zone between the two imaging zones.

As shown in FIG. 5, an intraocular lens 80, according to a preferred embodiment of the present invention, and which may be either an anterior or posterior chamber intraocular lens. Intraocular lens 80 comprises an optic 82, which may be refractive and monofocal, and first and second positioning (attachment) means or haptics 84 and 86 respectively that are attached or joined to opposite edge regions of the optic. Optic 82, a posterior surface 88 of which is shown, has an outside diameter, $D_1$, which is may, for example, be between about 5.5 mm and about 7.5 mm. Optic 82 is preferably constructed from an elastically deformable material, such as a silicone or acrylic material, to enable the folding of IOL 80 for implanting into an eye through a small ocular incision. Alternatively, optic 82 and haptics 84 and 86 may be formed from poly methyl methacrylate (PMMA).

Figure 6:
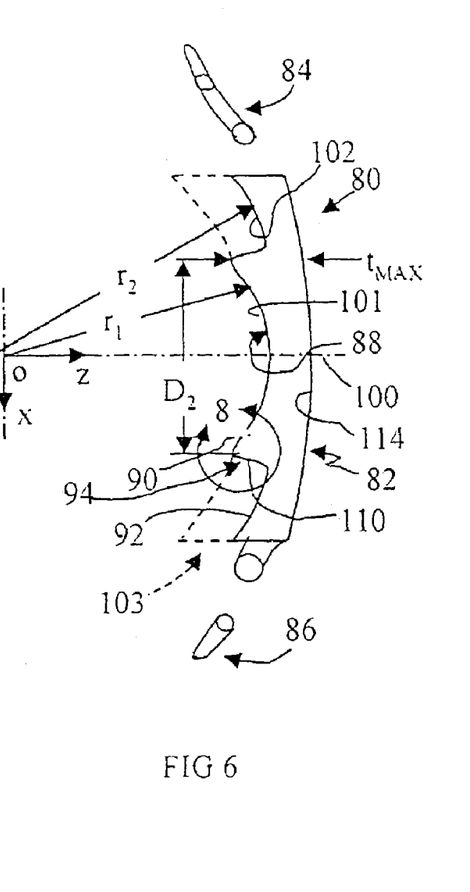
FIG. 6 is a longitudinal cross sectional view looking along line 6—6 of FIG. 5, showing the optic as a concave-convex (meniscus) optic, showing the first and second imaging zones and the transition zone therebetween forming the posterior surface of the optic, showing the second, outer imaging zone recessed into the optic relative to the first, central imaging zone and showing in phantom lines the thicker shape that the optic would be without the recessed second imaging zone.

In the cross sectional drawing of FIG. 6, optic 82 is shown as being of the concave-convex (meniscus) type. Posterior optic surface 88 is formed by respective first and second peri-axial, stepped imaging zones 90 and 92 that are separated by an annular transition zone 94 (shown by broken lines in FIG. 1). Imaging zones 90 and 92 are concentric with an optical axis 100 of optic 82 and both are shaped to have the same optical power, which is preferably outside the diopter range of between about −5 and about +5.

As further shown in FIG. 6, first imaging zone 90 has a preferred diameter, $D_2$, of between about 4.3 mm and about 4.5 mm and has a posterior surface 101 of radius, $r_1$, from an origin, O, located on optical axis 100. Second imaging zone 92 has a posterior surface 102 of radius r2, from coordinate origin, O. Second imaging zone 92 is shown recessed or stepped down relative to first imaging zone 90 with the effect of reducing the peripheral thickness of optic 82, a peripheral optic region 103, (shown in phantom lines) having been eliminated to thereby reduce the preferred maximum thickness, $t_{max}$, of optic 82 at any point to between about 0.3 mm and about 0.4 mm.

Figure 7:
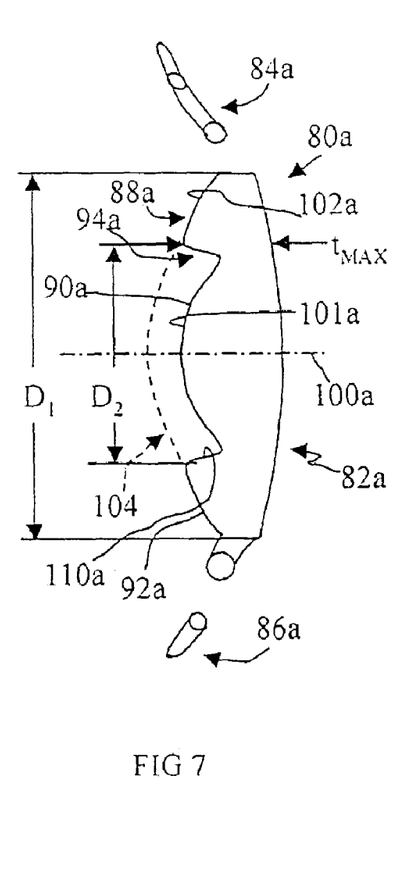
FIG. 7 is a longitudinal cross sectional view corresponding to FIG. 6, showing a variation optic as a bi-convex optic, showing the first and second imaging zones and the transition zone therebetween forming the posterior surface of the optic, showing the first, central, imaging zone recessed into the optic relative to the second imaging zone and showing in phantom lines the thicker shape that the optic would be without the recessed first imaging zone.

Alternatively, as depicted in the cross sectional drawing of FIG. 7, a refractive, monofocal optic 82a of an intraocular lens 80a (that corresponds to above-described intraocular lens 80), is of the bi-convex type. A posterior optic surface 88a is formed by respective first and second peri-axial, stepped imaging zones 90a and 92a that are separated by an annular transition zone 94a (corresponding to first and second imaging zones 90 and 92 and transition zone 94 shown in FIG. 2). Imaging zones 90a and 92a are concentric with an optical axis 100a of optic 82a and respective posterior surface regions 101a and 102a are shaped to have the same optical power, which is preferably outside the diopter range of between about −5 and about +5.

Optic 82a has the same outside diameter, $D_1$, that may be between about 5.5 mm and about 7.5 mm, and first imaging zone 90a has the same preferred diameter, $D_2$, of between about 4.3 mm and about 4.5 mm. First imaging zone 90a is, however, shown recessed or stepped down relative to second imaging zone 92a, with the effect of reducing the central thickness of optic 82a, a central optic region 104, (shown in phantom lines) having the effect of being eliminated to thereby reduce the preferred maximum thickness, $t_{max}$, of optic 82a at any point to between about 0.30 mm and about 0.40 mm.

For both optics 82 and 82a the use of only two concentric imaging zones 90, 92 and 90a, 92a, respectively, is preferred and is considered by the present inventor to provide a sufficiently narrow optic profile for safe implanting of IOLs 80 and 80a in anterior chambers of patients, while maintaining IOL optic integrity.

Considering optic 82 as being representative and as described below, the shape of the surface of transition zone 94 between first and second imaging zones 90 and 92 is important for reducing glare in a patient's eye from light impinging on optic 82.

Figure 8:
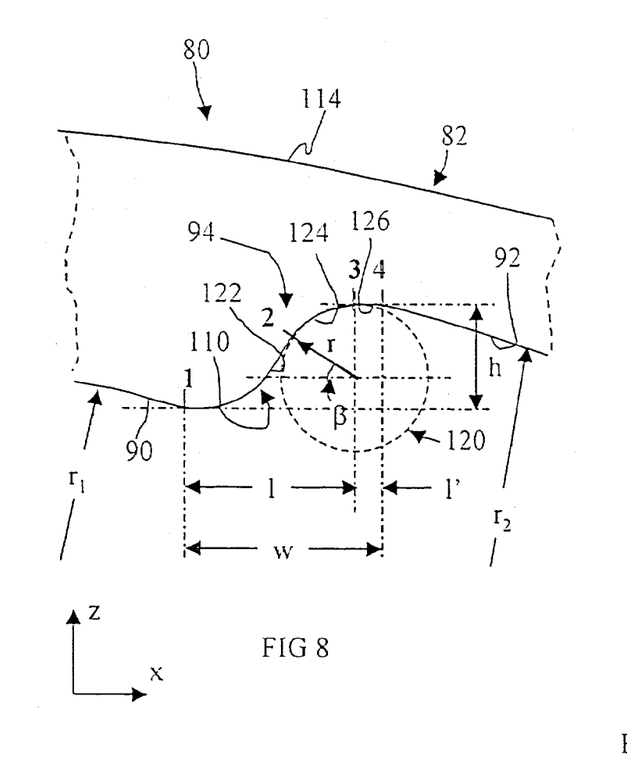
FIG. 8 is a an enlarged cross section of the transition zone of the intraocular lens optic of FIG. 6, showing the shape of a continuously variable curvature of the transition zone surface.

FIG. 8 shows, in an extremely enlarged representation, a preferred, transition zone surface 110 of transition zone 94 between respective first and second imaging zones 90 and 92 of IOL optic 82. Transition zone surface 110 is shown as being continuously variably curved, which reduces both indirect and direct glare in the eye of an individual in which IOL 80 is implanted, as more particularly described below.

As shown in FIG. 8, transition zone 94 has a total width, w, which is equal to combined widths, l, and, l' (described below), and a height (depth), h. Width, l, is preferably between about 1.5 times and about 2.0 times a radius, r, of a cutting tool 120 (shown in broken lines). A typical tool radius, r, may be about 0.125 mm, which is sufficiently large to achieve good optical quality of respective first and second imaging zones 90 and 92, while still being sufficiently small to produce a narrow transition zone 94. Accordingly, width, l, is preferably between about 0.14 mm and about 0.27 mm. Assuming, as described below, that width, l', is equal to about 0.1 times width, l, total transition zone width, w, (in the x direction) is preferably between about 0.15 mm and about 0.30 mm. Height, h, (in the z direction) of transition zone 94 is preferably between about 0.10 mm and about 0.40 mm.

As depicted in FIG. 8, transition zone curved surface 110 starts at point 1 at first imaging zone 90 and ends at point 4 at second imaging zone 92, with intermediate surface points 2 and 3.

Radius, $r_1$, of first imaging zone 90 (referring to FIG. 6) prior to point 1 is defined by the following mathematical expression:

$$z = \frac{U_1 X^2}{1 + \sqrt{1 - U_1^2 X^2}}, \quad (1)$$

and its derivative:

$$\frac{dz}{dX} = \frac{U_1 X}{\sqrt{1 - U_1^2 X^2}}, \quad (2)$$

$$\text{where } U_1 = \frac{1}{r_1}$$

is the surface curvature, and where z and x are the coordinates from origin, O (as indicated in FIGS. 6 and 8).

Point 2 at transition surface 110 is defined by width, 1 (from point 1 to the center of tool 120); transition zone height, h; tool radius, r; and tool angle, β, wherein angle, β, is preferably between about 15 degrees and about 20 degrees.

A transition zone surface region 122 between points 1 to 2 connects transition zone 94 with first imaging zone 90, and can be described by the polynomial form of third order as shown below:

$$z = A_1(X - x_1)^3 + B_1(X - x_1)^2 + C_1(X - x_1) + D_1, \quad (3)$$

and its derivative $$\frac{dz}{dX} = 3A_1(X - x_1)^2 + 2B_1(X - x_1) + C_1, \quad (4)$$

where $x_1$ equals the X coordinate at the edge of first imaging zone 90 (that is, half of first imaging zone diameter, $D_2$, shown in FIG. 6).

Point 3 at transition surface 110 is also defined by width, l; transition zone height, h; tool radius, r; and tool angle, β, which is preferably between about 15 degrees and about 20 degrees.

A transition zone surface region 124 between points 2 and 3 is defined by tool radius, r, according to the mathematical expression:

$$z = \frac{U(X - x_1 - l)^2}{1 + \sqrt{1 - U^2(X - x_1 - l)^2}} + C_2, \quad (5)$$

and its derivative:

$$\frac{dz}{dX} = \frac{U(X - x_1 - l)}{1 + \sqrt{1 - U^2(X - x_1 - l)^2}}, \quad (6)$$

$$\text{where } U = \frac{1}{r}$$

is the surface curvature

The Z coordinate at transition zone surface point 4 is preferably selected to have the same z value as at surface point 3. Width, l', of a surface region 126 between points 3 and 4 is preferably equal to about 0.10 times width, l, and provides a smooth continuity of transition zone 94 to second imaging zone 92.

Mathematical format of surface region 126 is the same as that of surface region 122 between surface points 1 and 2 and is given by the following expression:

$$z = A_3(X - x_1 - l)^3 + B_3(X - x_1 - l)^2 + C_3(X - x_1 - l) + D_3, \quad (7)$$

and its derivative:

$$\frac{dz}{dX} = 3A_3(X - x_1 - l)^2 + 2B_3(X - x_1 - l) + C_3 \quad (8)$$

Second transition zone 92 of radius, $r_2$, beyond transition surface point 4 is defined by the following mathematical expression:

$$z = \frac{U_2 X^2}{1 + \sqrt{1 - U_2^2 X^2}} + C_4, \quad (9)$$

and its derivative:

$$\frac{dz}{dX} = \frac{U_2 X}{\sqrt{1 - U_2^2 X^2}}, \quad (10)$$

$$\text{where } U_2 = \frac{1}{r_2}$$

is surface curvature

All coefficients $A_1$, $B_1$, $C_1$, $D_1$, $C_2$, $A_3$, $B_3$, $C_3$, $D_3$ and $C_4$ defining transition zone equations are calculated by a standard algebraic procedure for continuous border conditions between first imaging zone 90, each transition zone surface region and second imaging zone 92, that is, equal values for z and $$\frac{dz}{dX}$$

at each border between adjacent surface regions, and also using surface parameters l, l', h, r, $r_1$, and $r_2$.

Figure 9:
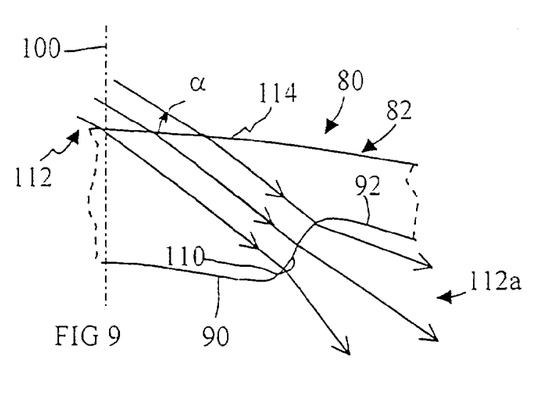
FIG. 9 is a cross sectional drawing similar to FIG. 8, depicting several light rays obliquely incident on the intraocular lens optic and showing the diverging of the light rays refracted by the optic through the transition zone surface.

FIG. 9, which is similar to FIG. 1, depicts a bundle of parallel light rays 112 impinging on anterior surface 114 of optic 82 at angle, α. Light rays 112 are refracted, in accordance with Snell's Law, as they enter, pass through and exit optic 82. However, because of the continuously variable curvature of transition zone surface 110 (FIG. 8), the light exits optic 82 as diverging rays 112a, rather than parallel rays as shown for rays 20a of the prior art Fresnel lens optic 24 depicted in FIG. 1. (Viewed image light rays are not shown to avoid confusion.)

Figure 10:
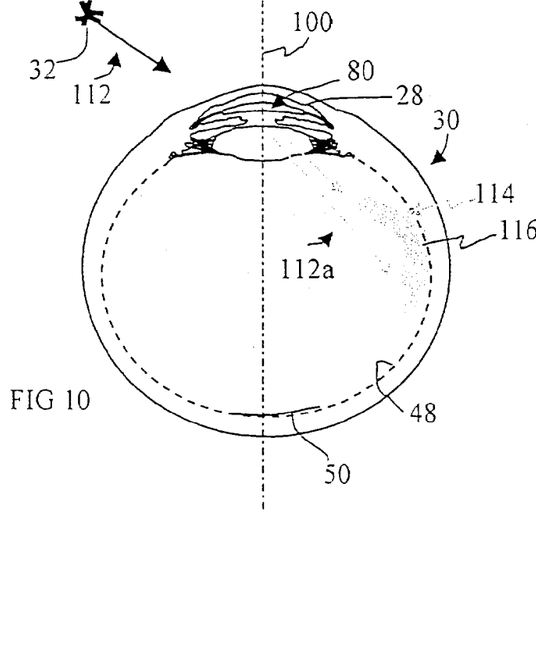
FIG. 10 is a cross sectional drawing of an eye, similar to FIG. 2, showing a diffuse indirect glare region caused by the light rays diverging from the transition zone surface as depicted in FIG. 9.

As depicted in FIG. 10, which corresponds to FIG. 2, diverging light rays 112a refracted from transition zone surface 110 of optic 82 impinge on a region 115 of retina 48 (shown in broken lines) of representative eye 30 to cause only a very diffused glare pattern 116 (indicated by dots). The result is that indirect glare in an individual's eye is greatly reduced by the non-abrupt, continuously variable curvature of transition zone surface 110, as compared to the indirect glare in an eye caused by flat surface 38 of abrupt Fresnel zone steps 40 of the same height.

Figure 11:
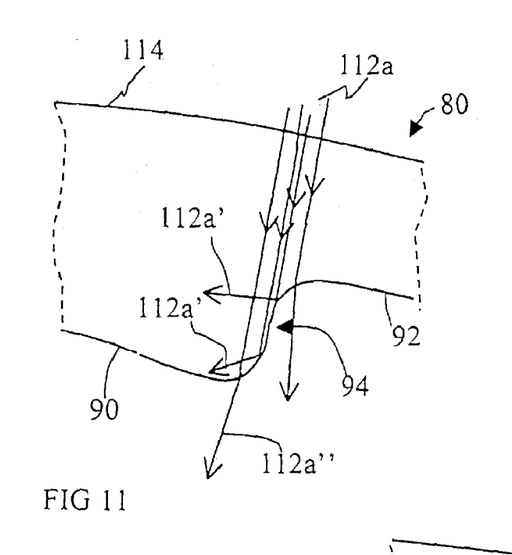
FIG. 11 is a cross sectional drawing similar to FIG. 9, depicting several direct light rays incident on the intraocular lens optic and depicting the redirecting of light out of the image by utilization of internal reflection at the transition zone surface.

FIG. 11 (which corresponds generally to FIGS. 8 and 9), depicts light rays 112a impinging perpendicularly onto optic anterior surface 114. Due to the particular shape of continuously variably curved transition zone surface 110, as described relative to FIG. 8, light rays 112a' are redirected at surface 110 out of the image by internal reflection.

Although a ray 112a" is depicted in FIG. 11 as refracted from surface 110 in a diverging manner that could cause some image glare, the glare is nevertheless substantially less than the direct glare caused by sharp corners 52 and 54 of Fresnel zone step 38 (FIG. 3) and other Fresnel zone steps of the same height.

The result of transition zone 94 having the continuously variable curved surface 110 described above, is that optic 82 of IOL 80 provided substantially less glare than sharp, flat Fresnel zone step(s) 38.

Also shown in broken lines, is a projected peripheral edge without the depicted transition zone, it is of course to be understood that the continuously variable curvature applied to surface 110 of transition zone 94 of optic 82 can also be applied to surface 110a of transition zone 94a of optic 82a (FIG. 7) with like glare reduction properties.

Figure 12:
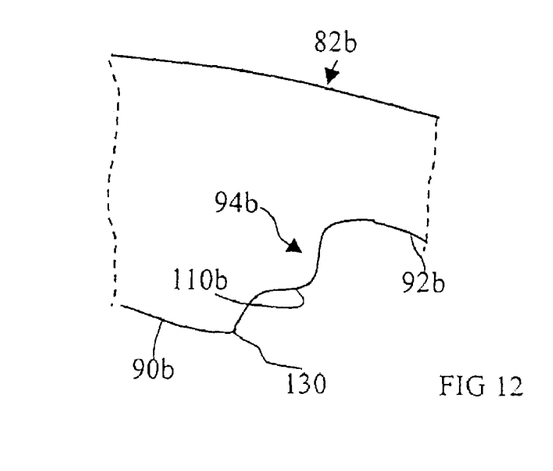
FIG. 12 is an enlarged cross sectional drawing, corresponding generally to FIG. 8, of a second variation transition zone of the intraocular lens optic of FIG. 6, showing the shape of a transition zone surface of variable curvature (instead of continuously variable curvature)
Figure 13:
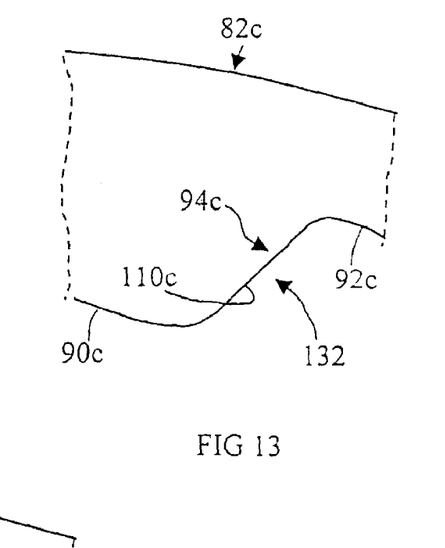
FIG. 13 is an enlarged cross sectional drawing, corresponding generally to FIG. 8, of a variation transition zone of the intraocular lens optic of FIG. 6, showing the shape of a transition zone surface of continuous curvature (instead of continuously variable curvature)

FIGS. 12 and 13 depict, in extremely enlarged representations, variation transition zone surface curvatures that although providing somewhat less glare reduction than the continually variable curvature described above for surface 110 of transition zone 94 of optic 82 nevertheless are within the scope of the present invention.

There is thus depicted in FIG. 12 a transition zone 94b between respective first and second imaging zones 90b and 92b of an optic 82b. As shown, imaging zones 90b and 92b may be identical to imaging zones 90 and 92 described above. Surface 110b of transition zone 94b is variably curved, but is not continuously variably curved as described above for transition zone surface 110, having, as an example, a discontinuity at a point 130. The variably curved region of transition zone surface 110b may be developed in a manner analogous to the above-described manner of developing transition zone surface 110 (FIG. 8)

A principal effect of variably curved transition zone surface 110b is that some direct glare may be caused by light diffraction at discontinuity point 130 in the manner depicted in FIGS. 3 and 4 for known Fresnel zone step 40.

There is depicted in FIG. 13 a transition zone 94c between respective first and second imaging zones 90c and 92c of an optic 82c. As shown, imaging zones 90c and 92c may be identical to imaging zones 90 and 92 described above. Surface 110c of transition zone 94c is shown continuously curved, but not continuously variably curved as described above for transition zone surface 110, having, as an example, a central region 132 of non-variable curvature a discontinuity at a point 130. The variably curved regions of transition zone surface 110c may be developed in a manner analogous to the above-described manner of developing transition zone surface 110 (FIG. 8)

A principal effect of continuously curved transition zone surface 110c is that some indirect glare may be caused by light refraction from region 132 of surface 110c in the manner depicted in FIGS. 1 and 2 for known Fresnel zone step 40.

Thus it can be seen from the foregoing that a narrow profile intraocular lens with glare reducing characteristics is provided.

Figure 14:
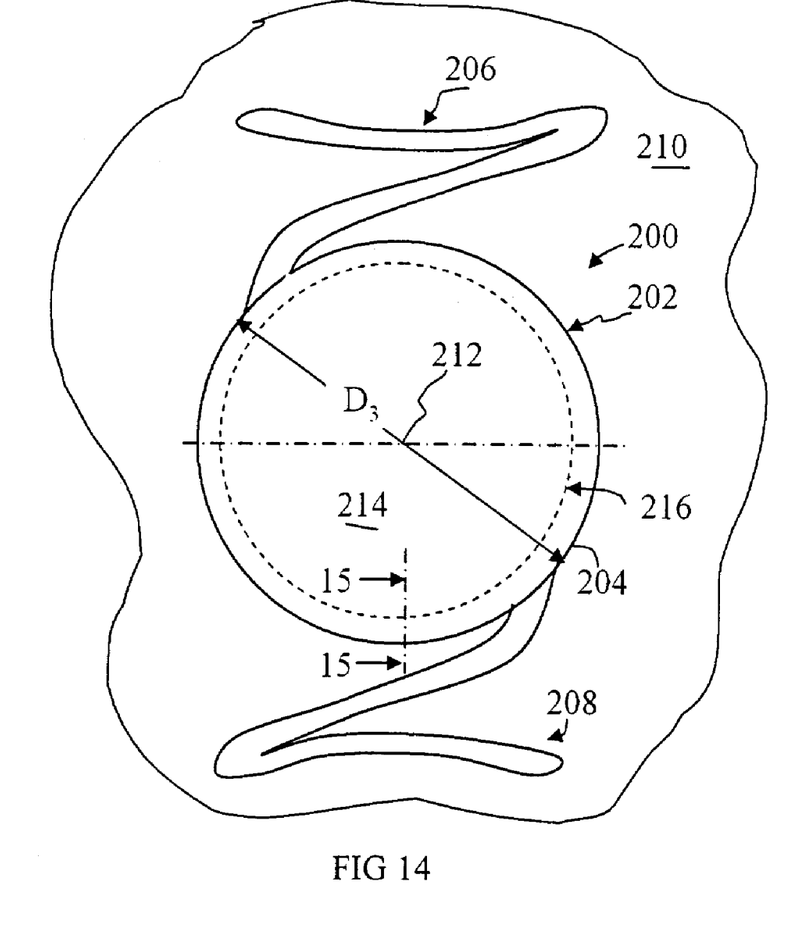
FIG. 14 is a plan view, similar to FIG. 5, of a narrow profile intraocular lens showing an optic having attached thereto, at opposite peripheral edges, attachment members (haptics) for securing the intraocular lens in an individual's eye, and showing in broken lines an annular peripheral edge region having a glare minimizing configuration in accordance with the present invention.

Description of FIGS. 14–18:

FIG. 14 is a plan view of a variation narrow profile (thin) intraocular lens (IOL) 200 comprising an optic 202, having a generally circular, glare reducing peripheral edge 204. First and second flexible attachment members (haptics) 206 and 208, respectively, are joined to opposite regions of optic edge 204 for supporting optic 202 in an individual's eye 210, with an optical axis 212 of the optic aligned with the optical axis of the eye. An anterior surface 214 of optic 202 is depicted. A peripheral edge glare reducing transition zone (described below) is indicated by an annular broken line 216.

Figure 15:
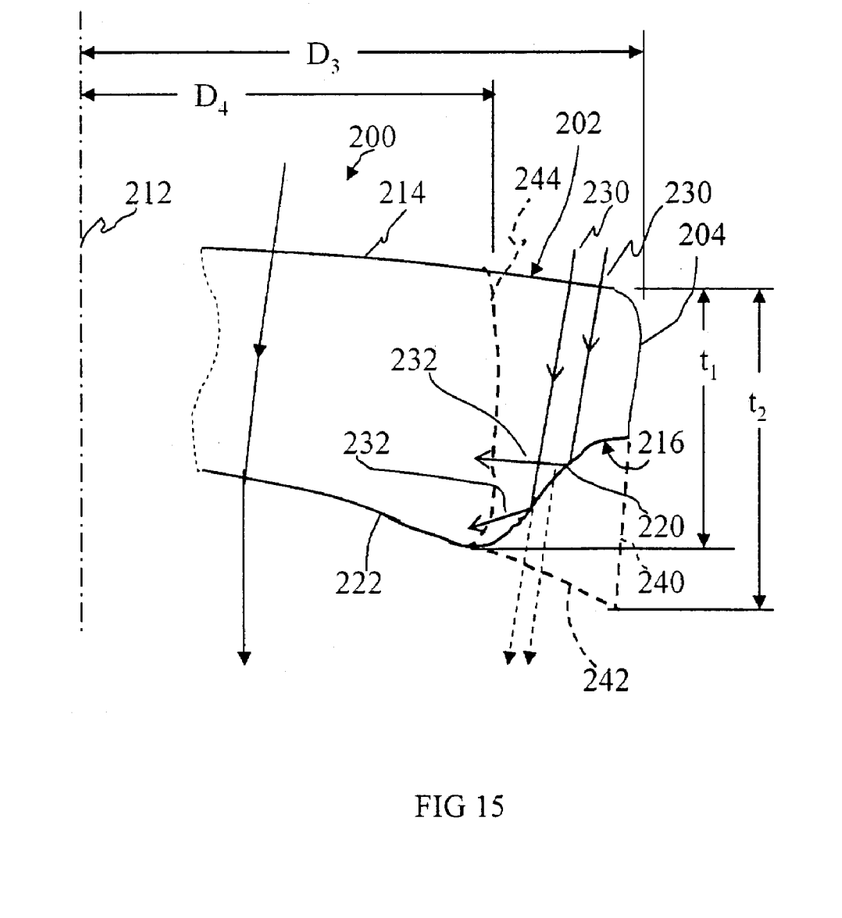
FIG. 15 is a cross sectional drawing taken along line 15—15 of FIG. 14, showing a peripheral edge transition zone having a surface of continuous curvature extending from a concave posterior surface of the optic, several direct light rays being shown as incident on the transition zone which is shaped for redirecting light out of the image location formed by the transition zone by utilization of internal reflection at the transition zone surface, so as to minimize direct glare in the eye of an individual in which the optic is implanted, also shown, in broken lines, is a projected peripheral edge without the depicted transition zone.

In the cross section of FIG. 15, peripheral, glare reducing transition zone 216 formed at optic peripheral edge 204 is shown having a surface 220 of continuous curvature, without any abrupt change in the surface curvature, that extends upwardly and outwardly from a concave optic posterior surface 222 toward convex optic anterior surface 214. Posterior surface 222 may be formed having an imaging zone not shown) centered at optical axis 212.

Light rays 230 are depicted as being directly (that is from the object viewed directly by the eye) incident on optic anterior surface 214 and impinge on a substantial width of transition zone surface 220 from inside optic 202. Light rays 230 impinging on transition zone surface 220 are internally reflected, as depicted by light rays 232, so as to minimize direct glare in eye 210 in which IOL 200 is implanted.

Because of edge transition zone 216, an edge thickness, $t_1$, of optic 202 is less than an edge thickness, $t_2$, resulting from a projection from the optic (without transition zone 216) by broken lines 240 and 242, thereby providing a thinner (narrower) optic 202 ($t_2-t_1$) than would otherwise result if the transition zone were not provided.

Alternatively, for optic 202 having an overall diameter, $D_3$, and a peripheral edge thickness, $t_1$, resulting from edge transition zone 216, it can be seen that for the same optic edge thickness, $t_1$, an optic for which transition zone 216 were not provided would have a smaller overall diameter, $D_4$, to a broken line 244 representing a projected optic peripheral edge. The result being that a larger diameter optic would be possible by providing edge transition zone 216 than would, for the same optic edge thickness, $t_1$, be provided without the transition zone. This larger diameter optic would result in reduced likelihood of edge glare because the optic edge 204 would be more prone to be outside the pupil opening under poor light conditions.

Figure 16:
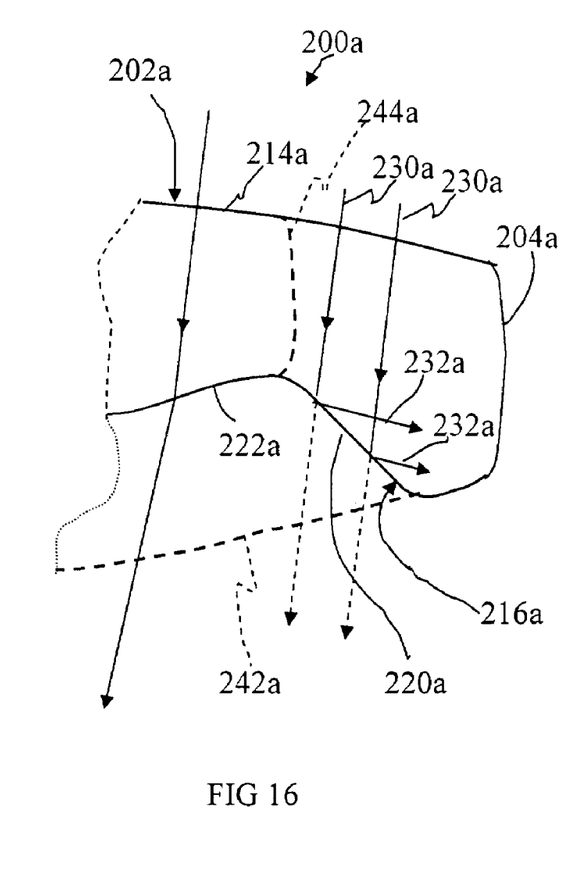
FIG. 16 is a cross sectional drawing, similar to FIG. 15, showing a peripheral edge transition zone having a surface of continuous curvature extending from a convex posterior surface of the optic, several direct light rays being shown incident on the transition zone which is shaped for redirecting light out of the image location formed by the transition zone by utilization of internal reflection at the transition zone surface, so as to minimize direct glare in the eye of an individual in which the optic is implanted, also shown, in broken lines, is a projected peripheral edge without the depicted transition zone.

FIG. 16 depicts a portion of a first variation IOL 200a which corresponds generally to IOL 200 of FIG. 15, except that a posterior surface 222a of an optic 202a is shown convex, instead of concave. For optic 202a, a transition zone 216a formed adjacent optic peripheral edge 204a has a surface 220a of continuous curvature without any abrupt change in said surface curvature and is shown extending downwardly and outwardly from posterior surface 222a toward edge 204a. As depicted, light rays 230a incident directly on optic anterior surface 214a impinge on a substantial width of transition zone surface 220a from inside optic 202a and are internally reflected as rays 232a, thereby minimizing direct glare in an individual's eye in which IOL 200a is implanted. A projected posterior surface of optic 202a, depicted by broken line 242a, shows the substantially greater central thickness of the optic that would be required for the same optic diameter without transition zone 216a being provided.

Figure 17:
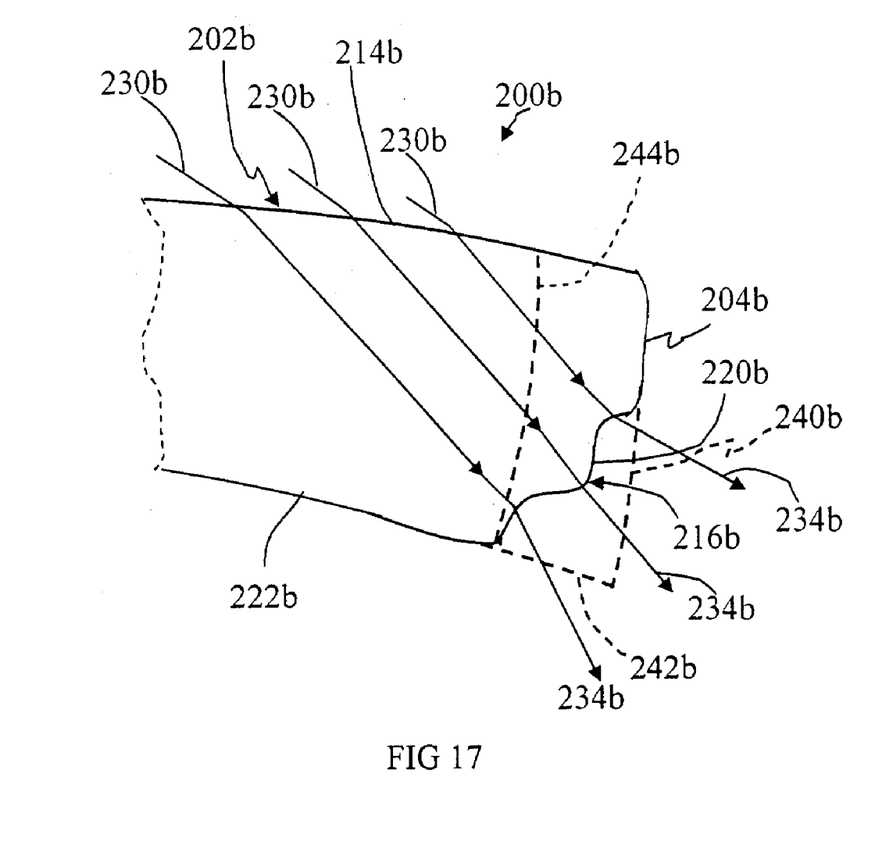
FIG. 17 is a cross sectional drawing, similar to FIG. 15, showing a peripheral edge transition zone having a surface of continuously variable curvature extending from a concave posterior surface of the optic, several direct light rays being shown incident on the transition zone which is shaped for refracting incident light out of the transition zone in a manner minimizing indirect glare in the eye of an individual in which the optic is implanted, also shown, in broken lines, is a projected peripheral edge without the depicted transition zone.

FIG. 17 depicts a second variation IOL 200b that corresponds directly to IOL 200 of FIG. 15, except that a transition zone 216b formed adjacent optic peripheral edge 204b extends upwardly and outwardly from concave posterior surface 222b of optic 202b to optic peripheral edge 204b. Transition zone 216b is formed having a non-linear surface 220b of continuously variable curvature that is shaped to minimize indirect glare in an individual's eye in which IOL 200b is implanted.

Light rays 230b obliquely incident on optic anterior surface 214b pass through optic 202b to impinge on a substantial width of surface 220b of transition zone 216b. Impinging rays 230b are refracted at transition zone surface 220b and exit transition zone 216b as rays 234b that diverge in a manner spreading the light at the eye retina and minimizing indirect glare in the individual's eye in which IOL 200b is implanted.

As described above relative to optic 202 (FIG. 15) for broken lines 240 and 242, broken lines 240b and 242b depict the projected extension of optic 202b in the absence of transition zone 216b, showing a projected thicker edge region. Alternatively, broken line 244b depicts a projected, reduced optic diameter edge associated with an optic thickness provided by transition zone 216b.

Figure 18:
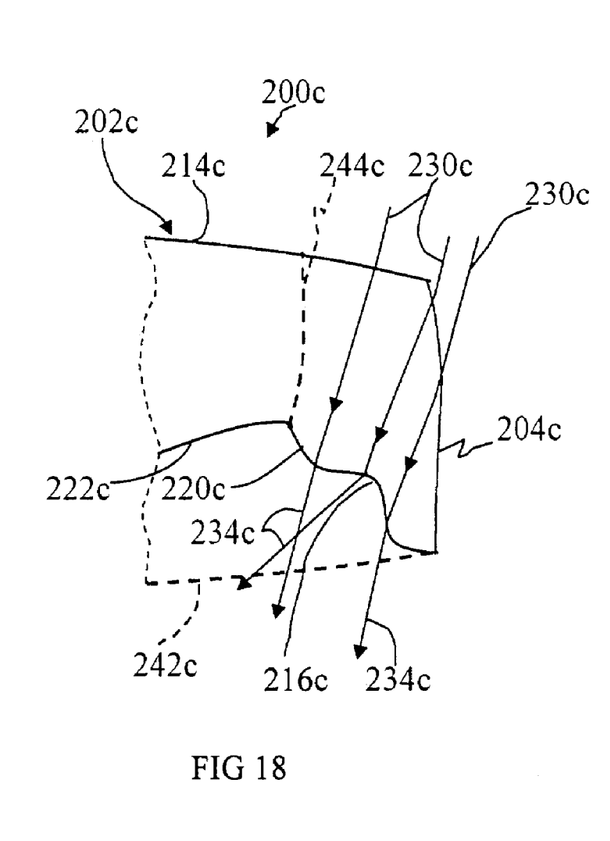
FIG. 18 is a cross sectional drawing, similar to FIG. 16, showing a peripheral edge transition zone having a surface of continuously variable curvature extending from a convex posterior surface of the optic, several direct light rays being shown incident on the transition zone which is shaped for refracting incident light out of the transition zone in a manner minimizing indirect glare in the eye of an individual in which the optic is implanted, also shown, in broken lines, is a projected peripheral edge without the depicted transition zone.

FIG. 18 depicts a third variation IOL 200c that corresponds generally to IOL 200b of FIG. 17. IOL 200c further corresponds directly to IOL 200a of FIG. 16, except that a transition zone 216c of optic 202c, adjacent optic peripheral edge 204c, extends downwardly and outwardly from convex posterior surface 222c of optic 202c and is formed having a non-linear surface 220c of continuously variable curvature (in addition to having continuous curvature) shaped to minimize indirect glare in an individual's eye in which IOL 200c is implanted.

Light rays 230c obliquely incident on optic anterior surface 214c pass through optic 202c and impinge on a substantial width of transition zone surface 220c. These impinging rays 230c are refracted by surface 214c and edge 204c exit transition zone 216c as rays 234c that diverge in a manner minimizing indirect glare in the individual's eye in which IOL 200c is implanted.

As described above relative to optic 202a (FIG. 16) for broken line 242a, broken line 242c depicts the projected extension of optic 202c in the absence of edge transition zone 216c, showing a projected thicker optic region. Alternatively, broken line 244c depicts a projected, reduced optic diameter edge associated with an optic central thickness provided by transition zone 216b.

It is evident from the foregoing that by providing the described optic transition zones 216 –216c for IOL optics 200–200c thickness (central or edge) of the optics can be minimized, while still providing relatively large diameter optics. This has been described as resulting from forming transition zones 216–216c with surfaces 220–220a of continuous curvature or with surfaces 22b–220c of continuously variable curvature so as to minimize direct glarer or indirect glare in an individual's eye in which IOLs 200–200c are implanted.

Although there has been described above a narrow profile intraocular lens with glare reduction and variations thereof for implanting in a narrow space, particularly in the anterior chamber, of a patient's eye, in accordance with the present invention for purposes of illustrating the manner in which the present invention may be used to advantage, it is to be understood that the invention is not limited thereto. Consequently, any and all variations and equivalent arrangements that may occur to those skilled in the applicable art are to be considered to be within the scope and spirit of the invention as set forth in the claims, which are appended hereto as part of this application.

What is claimed is:

1. A narrow profile, glare reducing, intraocular lens comprising:
   a. an anterior chamber optic having a convex anterior surface and a concave posterior surface, said optic having a peripheral edge and an optical axis;
   b. a transition direct glare minimizing zone between said posterior surface and said optic peripheral edge, said transition zone having a transition surface extending outwardly and posteriorly from the posterior surface, said transition surface being of continuous curvature without any abrupt change in transition surface curvature, the transition surface minimizing light transmission through the transition zone by causing internal reflection of light impinging on the optic from a centrally located source of light within a substantial width of said transition zone, the transition zone being in part thicker than the optic at the optical axis; and
   c. positioning means joined to said optic for positioning the optic in an eye with said optical axis of the optic generally aligned with an optical axis of the eye.

2. The narrow profile, glare reducing, intraocular lens as claimed in claim 1, wherein said posterior surface is formed having an imaging zone centered at the optical axis of the optic.

3. The narrow profile glare reducing, intraocular lens as claimed in claim 1 wherein a maximum optic thickness is less than about 0.5 mm.

4. The narrow profile glare reducing intraocular lens as claimed in claim 1, wherein the optic has a thickness enabling insertion into the anterior chamber of an eye.

* * * * *